(12) United States Patent
Jonas et al.

(10) Patent No.: US 10,470,686 B2
(45) Date of Patent: Nov. 12, 2019

(54) ACCESSIBLE MAGNETIC RESONANCE IMAGING SCANNER SYSTEM FOR MAGNETIC RESONANCE GUIDED INTERVENTIONAL PROCEDURES

(71) Applicant: KONINKLIJKE PHILIPS N.V., Eindhoven (NL)

(72) Inventors: Philip Alexander Jonas, Eindhoven (NL); Johannes Ferdinand Van Der Koijk, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 948 days.

(21) Appl. No.: 14/655,060

(22) PCT Filed: Dec. 12, 2013

(86) PCT No.: PCT/IB2013/060834
§ 371 (c)(1),
(2) Date: Jun. 24, 2015

(87) PCT Pub. No.: WO2014/102641
PCT Pub. Date: Jul. 3, 2014

(65) Prior Publication Data
US 2015/0346298 A1 Dec. 3, 2015

Related U.S. Application Data

(60) Provisional application No. 61/745,842, filed on Dec. 26, 2012.

(51) Int. Cl.
*A61B 5/055* (2006.01)
*G01R 33/30* (2006.01)
(Continued)

(52) U.S. Cl.
CPC .......... *A61B 5/0555* (2013.01); *G01R 33/307* (2013.01); *G01R 33/381* (2013.01);
(Continued)

(58) Field of Classification Search
CPC ............ A61B 5/0555; F04C 2270/041; G01R 33/307; G01R 33/3802; G01R 33/3806; G01R 33/381; G01R 33/385
(Continued)

(56) References Cited

U.S. PATENT DOCUMENTS

| | | |
|---|---|---|
| 5,307,039 A | 4/1994 | Chari et al. |
| 5,396,207 A | 3/1995 | Dorri et al. |

(Continued)

FOREIGN PATENT DOCUMENTS

| | | |
|---|---|---|
| JP | 63272335 | 9/1988 |
| JP | 03188830 A | 8/1991 |

(Continued)

*Primary Examiner* — Jay Patidar

(57) ABSTRACT

A magnetic resonance (MR) imaging system (100) including a housing (102) having first and second openings (110, 116), and first and second solenoid coils (160, 150), the first and second solenoid coils (160, 150) generate a magnetic field suitable for imaging within a region of interest (ROI). The first and second solenoid coils (160, 150) have a common longitudinal axis (LA). The first and second openings (110, 116) are situated on opposite sides of the housing (102) along the longitudinal axis (LA). The first solenoid coil (160) has a different inside diameter than the second solenoid coil (150) and is positioned adjacent the first opening (110). The second solenoid coil (150) is positioned adjacent the second opening (116). Accordingly, the system provides improved access to the patent during imaging, e.g. for MR guided interventional procedures.

20 Claims, 7 Drawing Sheets

(51) Int. Cl.
*G01R 33/38* (2006.01)
*G01R 33/381* (2006.01)
*G01R 33/385* (2006.01)

(52) U.S. Cl.
CPC ....... *G01R 33/3802* (2013.01); *G01R 33/385* (2013.01); *G01R 33/3806* (2013.01); *F04C 2270/041* (2013.01)

(58) Field of Classification Search
USPC .................................................. 324/318–322
See application file for complete search history.

(56) References Cited

U.S. PATENT DOCUMENTS

| | | | |
|---|---|---|---|
| 5,416,415 | A | 5/1995 | Dorri et al. |
| 5,677,630 | A | 10/1997 | Laskaris |
| 5,708,360 | A | 1/1998 | Yui |
| 5,801,609 | A | 9/1998 | Laskaris et al. |
| 5,810,006 | A * | 9/1998 | Votruba ................. A61B 5/055 324/318 |
| 5,914,600 | A | 6/1999 | Pulyer |
| 6,195,578 | B1 * | 2/2001 | Distler ................. A61B 5/0555 324/318 |
| 6,335,623 | B1 | 1/2002 | Damadian et al. |
| 6,462,548 | B1 | 10/2002 | Havens |
| 6,707,363 | B1 | 3/2004 | Abele |
| 6,806,712 | B2 * | 10/2004 | Akgun ................... A61B 5/055 324/309 |
| 7,148,689 | B2 * | 12/2006 | Huang ................. G01R 33/383 324/319 |
| 7,274,192 | B2 | 9/2007 | Havens |
| 7,466,133 | B2 * | 12/2008 | Havens .............. G01R 33/3815 324/319 |
| 7,680,525 | B1 * | 3/2010 | Damadian ........... A61B 5/0555 324/318 |
| 7,697,971 | B1 | 4/2010 | Green et al. |
| 2002/0013524 | A1 * | 1/2002 | Hayashi ............. G01R 33/3806 600/410 |
| 2003/0016018 | A1 * | 1/2003 | Arz .................... G01R 33/3854 324/322 |
| 2003/0094947 | A1 | 5/2003 | Akgun |
| 2004/0021467 | A1 * | 2/2004 | Eberler ............ G01R 33/34007 324/318 |
| 2006/0055406 | A1 | 3/2006 | Lvovsky et al. |
| 2007/0145979 | A1 * | 6/2007 | Roland ................ A61B 5/0555 324/319 |
| 2007/0241754 | A1 * | 10/2007 | Hirata .............. G01R 33/56563 324/312 |
| 2009/0171185 | A1 | 7/2009 | Chou et al. |
| 2010/0329414 | A1 * | 12/2010 | Zhu ........................ A61N 5/10 378/4 |
| 2012/0066895 | A1 * | 3/2012 | Tsuda ................... A61B 5/055 29/602.1 |

FOREIGN PATENT DOCUMENTS

| | | |
|---|---|---|
| JP | 2004337240 A | 12/2004 |
| JP | 2007301295 A | 11/2007 |
| WO | 9735206 | 9/1997 |

* cited by examiner

ACCESSIBLE MAGNETIC RESONANCE IMAGING SCANNER SYSTEM FOR MAGNETIC RESONANCE GUIDED INTERVENTIONAL PROCEDURES

CROSS-REFERENCE TO PRIOR APPLICATIONS

This application is the U.S. National Phase application under 35 U.S.C. § 371 of International Application No. PCT/IB2013/060834, filed on Dec. 12, 2013, which claims the benefit of U.S. Patent Application No. 61/745842, filed on Dec. 26, 2012. These applications are hereby incorporated by reference herein.

The present system relates to a nuclear magnetic resonance imaging (MRI) system and, more particularly, to an accessible MRI system suitable for MR guided interventional (MRGI) procedures and a method of operation thereof.

Typically, MRGI procedures rely upon magnetic resonance imaging (MRI) systems to obtain real-time images of portions of body of a patient within a region of interest (ROI) which includes a scanning region of the MRI system. Then, using the real-time images, a surgeon may perform an interventional procedure with increased accuracy. With regard to MRI systems, these systems typically include closed and open types. Both of these systems typically incorporate main coils made up of a superconducting material (e.g., superconducting coils) to generate highly uniform magnetic fields within the ROI.

With regard to the closed-type MRI systems, these systems typically employ main coils which have an elongated center bore which is open and in which the ROI is located. While these main coils produce a highly uniform (e.g., homogenous) magnetic field at the ROI, the ROI is located deep within the opening of the center bore which impedes access to portions of the patient such as at the ROI. This makes it is difficult, if not totally impossible, to perform MRGI procedures on patients in vivo using conventional closed type MRI systems.

With regard to the open-type MRI systems, these systems typically include planar- and split-type MRI systems both of which employ superconducting main coils which define a center bore. However, unlike the closed-type MRI systems, in the open-type MRI systems, the ROI is generated outside of the center bore of the superconducting main coils. For example, with regard to the planar-type MRI systems, the ROI is located above the center bore of the superconducting main coils as illustrated in U.S. Pat. No. 7,274,192, the entire contents of which are incorporated herein by reference. Accordingly, in planar-type MRI systems, the ROI, and, therefore, the patient, are located outside of the superconducting main coils. With regard to the split-type MRI systems, these systems typically include symmetric superconducting main coils which are placed axially apart from each other at a split by some distance so as to form a split region in which the ROI is located as illustrated by U.S. Pat. No. 7,274,192, the entire contents of which are incorporated herein by reference. In this system, access to the ROI is from the split region. Accordingly, the patient is located at least partially in the split region during use. While the open-type MRI systems may provide enhanced access to the patient at the ROI when compared to the closed-type MRI systems, they are costly, inefficient and/or have limited power (e.g., 0.5 Tesla (T)). Accordingly, a more efficient MRI system for performing MRGI procedures is desirable.

The system(s), device(s), method(s), user interface(s), computer program(s), etc. (hereinafter each of which will be referred to as system, unless the context indicates otherwise), described herein address problems in prior art systems.

In accordance with embodiments of the present system, there is disclosed a magnetic resonance (MR) imaging system suitable for MRGI procedures, the MR imaging system including a housing having first and second openings, and first and second solenoid coils, the first and second solenoid coils configured to generate a magnetic field suitable for imaging within a region of interest. The first and second solenoid coils may have a common longitudinal axis. The first and second openings are situated on opposite sides of the housing along the longitudinal axis. In accordance with embodiments of the present system, the first solenoid coil has a different inside diameter than the second solenoid coil and is positioned adjacent the first opening. The second solenoid coil is positioned adjacent the second opening.

A patient support may be situated within the first and second openings of the housing to insert a patient into the ROI. The patient support may articulate in one or more directions under the control of a controller. The first opening may be larger than the second opening. The patient support may include a further patient support situated at least in part within the first opening and having a bifurcated end extending from the first opening.

The housing may have a length, an exterior periphery defined by an exterior wall, and an interior opening defined by first, second and third interior walls, where the first and second interior walls each have a different inside diameter with the third interior wall radially extending between the first and second walls. The apparatus may include at least one gradient coil, situated adjacent to the third interior wall.

A controller may control patient positioning in coordination with image reconstruction. A display may be situated within the interior of the housing to render procedure related information. The at least one gradient coil may be an asymmetric gradient coil situated between at least one of the solenoid coils and the patient.

In accordance with embodiments of the present system, there is disclosed a solenoid structure for a magnetic resonance (MR) imaging system, including a closed solenoid structure having first and second openings and including first and second solenoid coils each having a common longitudinal axis to provide a homogenous magnetic field for imaging in a region of interest (ROI). The first and second openings may be situated on opposite sides of the closed solenoid structure along the longitudinal axis and may have different diameters. The first solenoid coil may have a different inside diameter than the second solenoid coil and may be positioned adjacent the first opening. The second solenoid coil may be positioned adjacent the second opening. The closed solenoid structure having a length extending along the common longitudinal axis, and an "L" shaped cross section. The first and second openings may have a circular cross section in a plane perpendicular to the longitudinal axis. A patient support may position a patient into a desired position of a plurality of positions under the control of a controller.

The present system is explained in further detail, and by way of example, with reference to the accompanying drawings wherein.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques and methods are omitted so as not to obscure the description of the present system. It should be expressly understood that the drawings are included for illustrative purposes and do not represent the scope of the present system. In the accompanying drawings, like reference numbers may designate similar elements, portions of similar elements and/or elements with similar functionality.

Figure 1A:
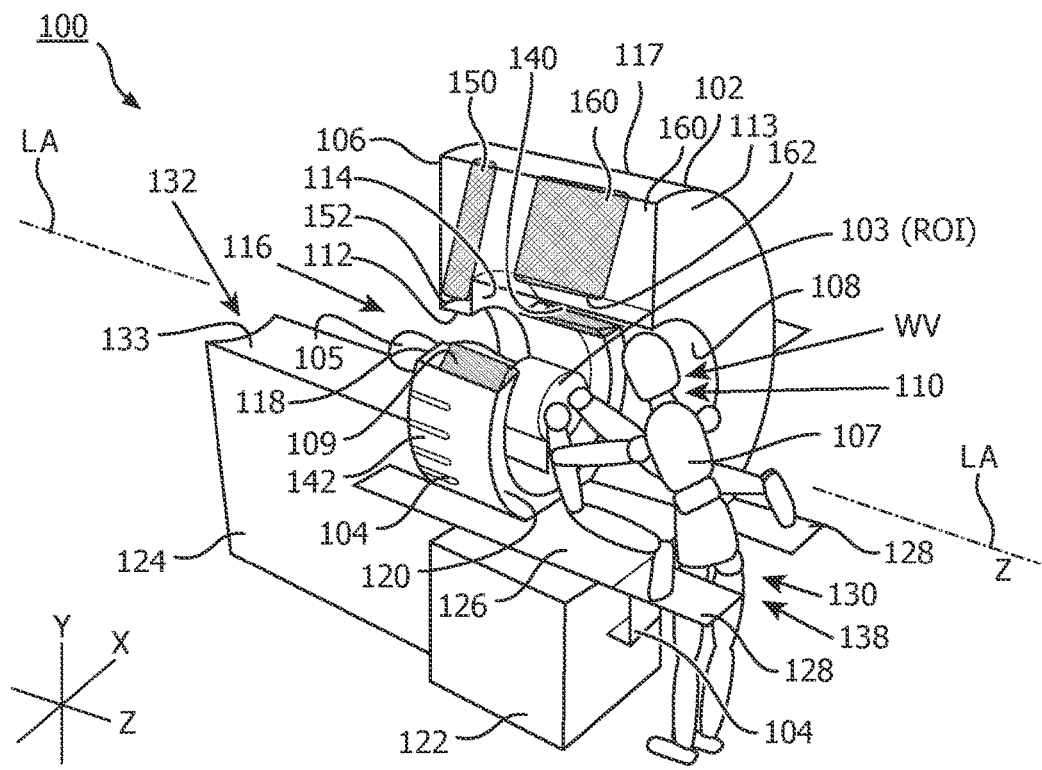
FIG. 1A is a partially cutaway perspective view of a portion of an MRI scanner in accordance with one or more embodiments of the present system.
Figure 2:
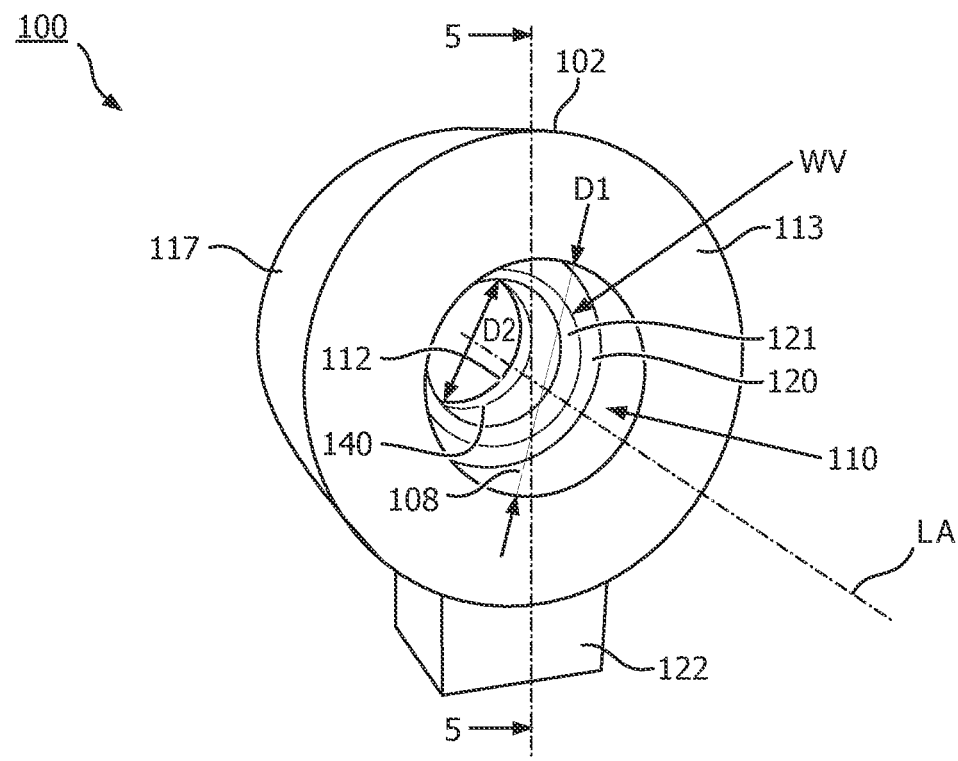
FIG. 2 is a partially elevated front perspective view of a portion of the MRI scanner system in accordance with one or more embodiments of the present system.

FIG. 1A is a partially cutaway perspective view of a portion of an MRI scanner 100 in accordance with one or more embodiments of the present system. The MRI scanner 100 may include one or more of housings 102, 104, a support 122, gradient coils as known in the art and a patient support 132. The housing 102 may contain two or more coil portions (e.g., a first coil portion 150 and a second coil portion 160). In accordance with further embodiments of the present system, the housing 102 may include more that two coil portions. For example, the housing may contain six to ten coil portions such as by counting partial winding as separate coils. For the sake of simplifying the following discussion, only first and second coil portions 150, 160 will be discussed further although the following description should be understood to include embodiments with more that two coil portions. The housing 104 may contain one or more gradient coil portions although to simplify the discussion herein, only one gradient coil 109 will be discussed herein although the following description should be understood to include embodiments with two or more gradient coil portions. FIG. 2 is a partially elevated front perspective view of a portion of the MRI scanner system in accordance with one or more embodiments of the present system.

Regarding FIGS. 1 and 2, in accordance with one or more embodiments of present system, the housing 102 may include one or more of first and second coil portions 150, 160, respectively, and includes first and second openings 110 and 116, respectively situated at opposite ends along a longitudinal axis (LA) of the housing 102. In accordance with one or more embodiments of the present system, the first and second openings 110 and 116 (apertures) are asymmetric in that one opening (e.g., opening 110) is larger than another of the openings (e.g., opening 116). Similarly, an inside diameter 152 (e.g., radius extending from the LA) of the first coil portion 150 may be larger than an inside diameter 162 of the second coil portion 160. Outside diameters of the first and second coils portions 150, 160 may be the same or difference in accordance with one or more embodiments of the present system.

In this way, the first opening 110 may be shaped and sized to provide access to a working volume WV for a user 107, such as a professional (e.g., a surgeon, a technician, a nurse, etc.), to access a patient 105 in at least a region of interest (ROI) 103 during a MRGI procedure and/or may be sized and shaped to provide access for the patient 105 to be positioned within the MRI scanner 100. In accordance with embodiments of the present system, the second opening 116 may be smaller than the first opening 110 and may be shaped and/or sized to enable positioning of the patient 105 so that at least portions of the patient 105 may be situated within the ROI. In accordance with one or more embodiments of the present system, the first and second openings 110, 116 may be circular, such as having a round cross section. In accordance with further embodiments of the present system, the openings 110, 116 may be other than circular (e.g., ovular, square shaped, a non-rotation symmetric shape, etc.) though in accordance with one or more embodiments of the present system, the first and second coils 150, 160 within the housing 102 may have a circular cross-section around the LA.

The support 122 may support the housings 102, 104 and may be articulable with one, two or more degrees of freedom. In accordance with embodiments of the present system, the support 122 may be articulable with six or more degrees of freedom so as to position the housings 102, 104, or portions thereof, in one or more desired positions. One or more actuators (hydraulic, electronic, pneumatic, mechanical, etc.) for example within the support 122 may be configured to operate under the control of a controller of the MR scanner system 100 to position one or more of the housings 102, 104 and/or the patient support 132, or parts thereof, in one or more desired positions under the control of the controller and/or a user such as the user 107. Accordingly, position and/or orientation of the housings 102, 104 and/or patient support 132 may be adjusted in one, two or more axes so that the patient 105 may be suitably positioned and the user 107 may conveniently access the patient 105 at the ROI 103 and/or other locations during use.

The patient support 132 may include one or more of a first patient support 133 and a second patient support 126 one or more of which may be configured to be articulated manually and/or under the control of the controller. The first and second patient supports 133 and 126, respectively, may include a table or anatomical support to support one or more body parts of the patient 105. Accordingly, one or more of the first and second patient supports 133 and 126, respectively, may include actuators (e.g., including locomotion devices, such as linear and/or rotary motors, etc.), and/or supports such as linear and/or rotary guides (e.g., linkages such as rotary and/or linear linkages, etc.) which may operate exclusively and/or mutually with each other to position the first and/or second supports 133 and 126, respectively, in a desired position. Further, the second patient support 126 may include an opening 130 such as a notch 138 situated between bifurcated ends 128 configured to support the patient 105 and/or enable positioning of the user 107. The opening 130 may be configured to receive the user 107 so that the user 107 may access the WV, when desired. Further, in some embodiments of the present system, it is envisioned that the first and/or second supports 133 and 126 may be removable, reconfigurable, changeable (e.g., by type of surgical procedure, desire to include bifurcated ends 128, etc.), or entirely absent.

Figure 1B:
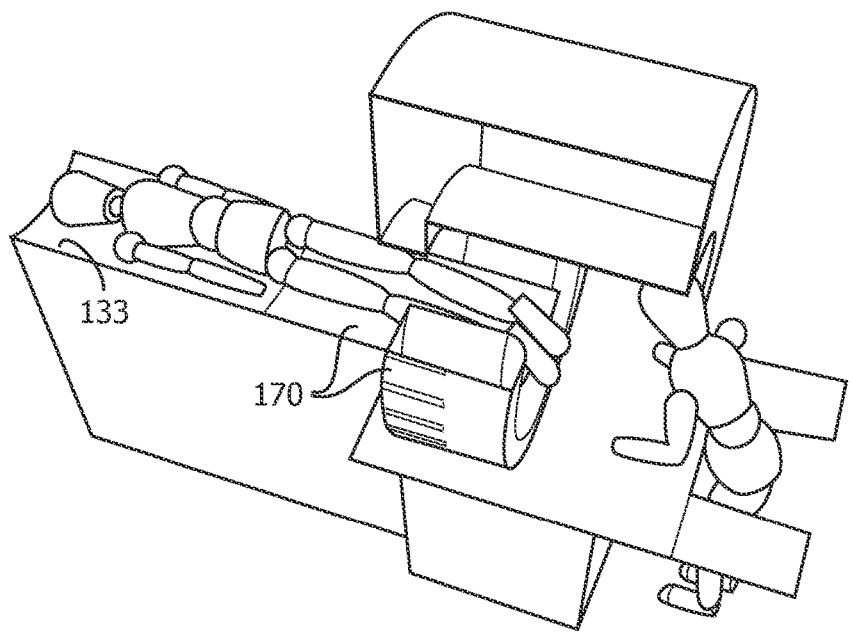
FIG. 1B is partially cutaway perspective view of a portion of an MRI scanner showing illustrative details of a patient support in accordance with one or more embodiments of the present system.
Figure 1C:
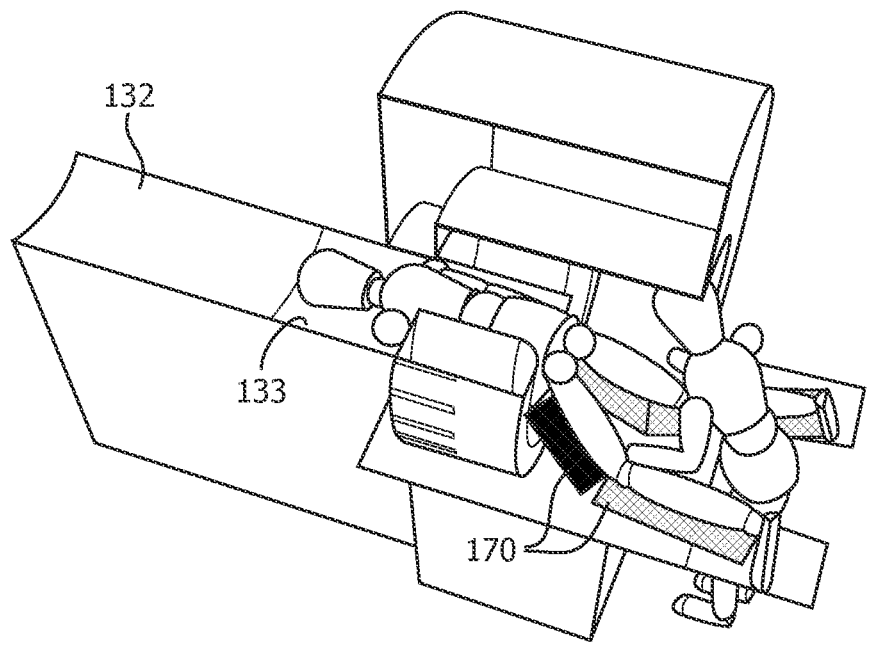
FIG. 1C is partially cutaway perspective view of a portion of an MRI scanner showing illustrative details of a patient support in accordance with one or more embodiments of the present system.

FIGS. 1B, 1C are partially cutaway perspective views of a portion of an MRI scanner 100 showing illustrative details of the first patient support 133 in accordance with one or more embodiments of the present system. The first patient support 133 may include one or more articulating sections 170 and may be slidable along the patient support 132 for purposes of positioning the patient 105 as shown. The first patient support 133 and articulating sections 170 may be positioned by actuators under the control of the controller and/or may simply have articulating joints, such as hinged joints, that are articulated based on the position of the first patient support 133 on the patient support 132. In accordance with one or more embodiments of the present system, the first patient support 133 and articulating sections 170 may be positioned manually, such as by manual positioning as desired. For example, the patient support 133 may be manually slidable into a desired position. In other embodiments, the patient support 133 may have casters, slides or other systems for sliding (e.g., manually, by actuators, through operation of the controller, etc.) the patient support 133 into a desired position, such as over the patient support 132.

The MRI scanner system 100 may include a user interface (UI) with which a user may interact with the system 100. The UI may include a user input device (e.g., a mouse, a keyboard, a touchscreen, a touchpad, a, microphone, for example for receiving audio commands, a trackball, a pointing device, etc.) which may receive user inputs. The controller may then process the user inputs and perform corresponding actions. For example, the user 107 may input a voice command to move the patient support 133 for example in a z direction along the patient support 132 for example and the controller may control the actuators to position the patient 105 accordingly. Further, the support 122 and/or patient support 132, may include one or more sensors (e.g., position sensors such as rotary and/or linear position sensors, etc.) which may determine a position of one or more of the housings 102, 104 and/or patient support 132, or parts thereof, and may provide corresponding sensor information to the controller so that the controller may determine corresponding positions and/or may control the actuators accordingly. In yet other embodiments, it is envisioned that one or more of the housings 102, 104 may include position sensors for identifying a position of one or more of the housings 102, 104 and the patient 105.

The housing 102 may have an outer wall 117 situated between first and second end walls 113 and 106, respectively, and first, second, and third, interior walls 108, 112, and 114, respectively, situated between the first and second end walls 113 and 106. Further, the housing 102 may have a length defined by first and second end walls 113 and 106, respectively (e.g., such as between the first and second end walls 113 and 106, up to respectively exterior walls, etc.). The housing 102 may define an interior cavity 115 situated between the outer wall 117, the first and second end walls 113 and 106, respectively, and the first, second, and third, interior walls 108, 112, and 114, respectively.

The first and second coil portions 150, 160 may be positioned within the housing 102 and may be configured to generate at least part of a magnetic field in at least a portion of a scanning volume such as the ROI 103. For example, the first conducting coil portion 150 may be positioned within the interior cavity 115 that is partially bounded by the walls 117, 106, 112, 114. The second conducting coil portion 160 may be positioned within the interior cavity 115 that is partially bounded by the walls 117, 113, 108. Accordingly, the first and second coil portions 150, 160 may include one or more current conducting coils and/or magnets situated in the interior cavity 115. The current conducting coils may include coils formed from super- and/or non-superconducting materials.

The first and second coil portions 150, 160 may have a longitudinal axis which corresponds with the longitudinal axis (LA) of the housing 102. The first interior wall 108 may have a diameter d1 and the second interior wall 112 may have a diameter d2 which is smaller than d1 (e.g., see FIG. 2). The third interior wall 114 may extend between the first and second interior walls 108 and 112, respectively. Accordingly, the third interior wall 114 may form at least part of a flange. Further, the third interior wall 114 may extend in a radial direction relative to the longitudinal axis LA. However, other directions are also envisioned in accordance with embodiments of the present system.

The housing portion 104 may include the gradient coil 109 within a cavity formed by the housing portion 104 as shown. The housing 104 may include first and second end walls 120 and 118, respectively, the cavity, and a center opening. The housing portion 104 may include an interior wall 140 and an exterior wall 142 situated between the first and second end walls 120 and 118, respectively. The first and second end walls 120 and 118, respectively, may define a length of the gradient coil 109 and the interior wall 140 may define the center opening. The interior wall 140 may have a shape and/or a size which is similar to the shape and/or size of the first interior wall 108 of the housing 102. Accordingly, the interior wall 140 may have a diameter d3 which is substantially equal to the diameter d1 of the first interior wall 108 of the first coil 102 as will be described below. The first and second end walls 120 and 118, respectively, may extend between the interior wall 140 and an exterior wall 142. The housing 104 may be shaped and/or sized to fit within the center opening of the housing 102 adjacent to the third interior wall 114 of the housing 102. Accordingly, for example, the exterior wall 142 of the housing 104 may have a shape which is the substantially similar to the first interior wall 108 of the housing 102 and may have a diameter d3 which is smaller than the diameter d1 (e.g., slightly smaller, such as +/−10% of diameter d1, +/−5% of diameter d1, +/−1% of diameter d1, +/−0.5% of diameter d1, etc.) of the first interior wall 108 of the housing 102. However, with regard to length, the length of the housing 104 should be less than the distance between the third interior wall 114 and the first end wall 113 of the housing 102 (e.g., significantly less, such as +/−40% of length, +/−20% of length, +/−10% of length, +/−1% of length, etc.) so as form a working volume (WV) within the housing 102, wherein the WV may be defined as a space situated within the first interior wall 108 of the housing 102 which lies between the end wall 120 of the housing 104 and first end wall 113 of the housing 102. Thus, the length of the housing 104 may be significantly less than the length of the housing 102.

Similarly to the first coil portion 150, the second coil portion 160 is configured to generate a magnetic field to provide at least part of a magnetic field in at least a portion of a scanning volume such as the ROI 103. Accordingly, the first and second coil portions 150, 160 may include one or more current conducting coils and/or magnets situated within the housing 102. The current conducting coils may include coils formed from super- and/or non-superconducting materials.

To access the working volume WV, a user such as the user 107 may access the WV through the first opening 110. Further, the patient 105 may controllably (e.g., under the control of the controller) enter the ROI from either of the first opening 110 and/or the second opening 116. Accordingly, the patient support 132 may be configured to controllably insert the patient 105 into the ROI via either of the first and second openings 110, 116, for example as shown in FIGS. 1B, 1C.

FIG. 2 is a partially elevated front perspective view of a portion of the MRI scanner system 100 in accordance with embodiments of the present system. The first opening 110 is situated in the first end wall 113 of the housing 102. The first end wall 120 of the housing 104 may include a rounded, tapered, beveled and/or chamfered portion 121 to facilitate user access. In this view, the patient support 132 has been removed for the sake of clarity. Further, the housings 102 and 104, respectively, may be circular in cross section. The longitudinal axis LA may extend through the center openings of the housings 102 and 104, respectively as illustratively shown in the figure or may be offset from the longitudinal axis.

Figure 3:
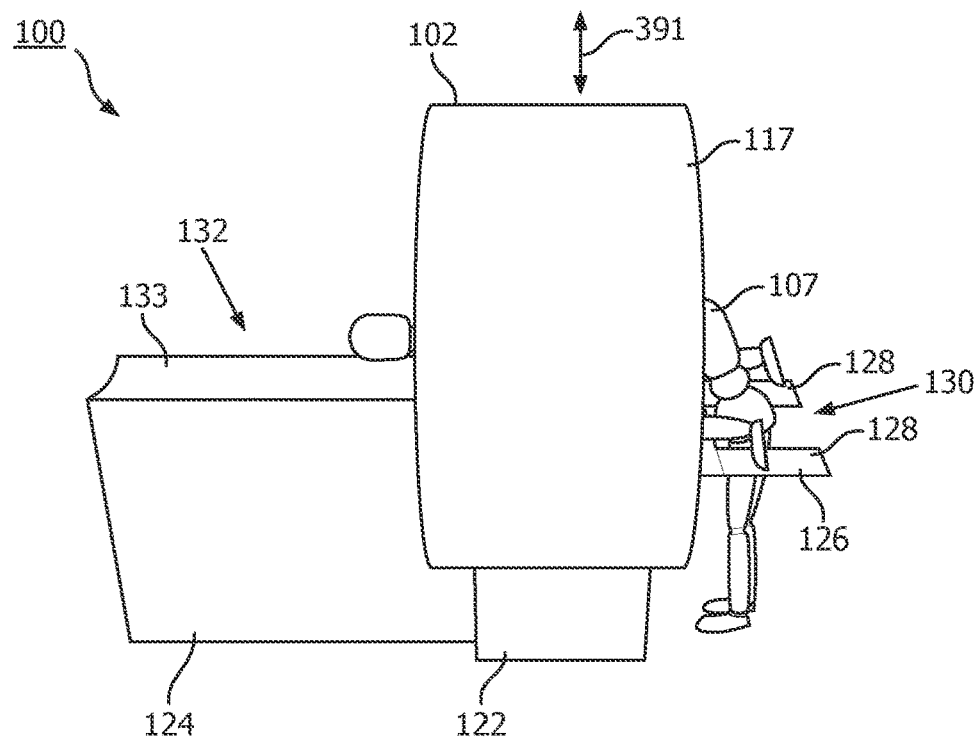
FIG. 3 is a partially elevated side perspective view of a portion of an MRI scanner system in accordance with one or more embodiments of the present system.

FIG. 3 is a partially elevated side perspective view of a portion of an MRI scanner system 100 in accordance with embodiments of the present system. The support 122 may raise and/or lower the housing 102 and the support 124 may raise and/or lower the patient support 132/133 as illustrated by arrow 391. However, in yet other embodiments, either of the support 122 or support 124 may be fixedly located.

Figure 4:
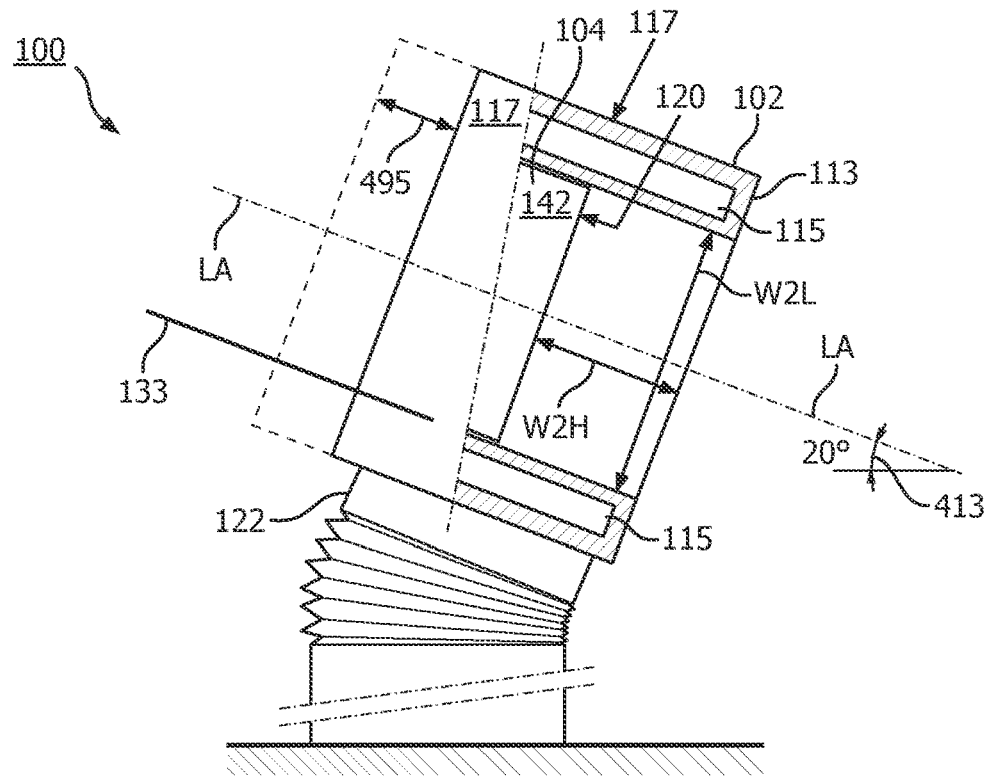
FIG. 4 is a cutaway side perspective view illustration of a portion of the MRI scanner system shown in a tilted orientation in accordance with one or more embodiments of the present system.

FIG. 4 is a cutaway side perspective view illustration of a portion of the MRI scanner system 100 shown in a tilted orientation in accordance with one or more embodiments of the present system. The scanner system 100 may be tilted relative to a reference point, plane (e.g., x-z plane, x-y plane, or y-x plane), or axis (e.g., −10 degrees rotation about the x axis relative as illustrated by arrow 493). Further, the housing 102 may be moved linearly along the longitudinal axis LA as illustrated by arrow 495. The controller may control the support 122 and/or the patient support 133 to tilt and/or move the housing 102 and/or the patient support 133 to a desired position and/or orientation in accordance with stored settings and/or inputs of the user 107. For example, with respect to stored settings the system may store several patient orientation settings in a memory of the system in accordance with a default setting (e.g., horizontal=0 degrees of tilt, etc.), a particular user (e.g., Dr. A: 0 degrees of tilt at 4.5 feet longitudinal axis (center) height; Dr. B: 5 degrees of positive tilt, 5.0 feet longitudinal axis (center) height, etc.), a patient, a previously stored setting, a particular type of procedure (e.g., cervical procedures 4.5 degrees positive tilt, cranial procedures 7 degrees tilt, etc.). Accordingly, the system may include a routine via a user interface (UI) to enter a user's name (e.g., Dr. A), a procedure type, a patient identification or other information, etc., and the controller may obtain corresponding settings from a memory of the system. The controller may then control the actuators of the support 132 to position the patient support 133 in accordance with the corresponding settings. Position sensors may detect position information related to positions of one or more portions of the support 132 and may provide this information to the controller. The controller may then control the actuators of the support 132 accordingly.

With regard to user inputs, the user 107 may enter a desired position command such as related to a desired position and/or orientation. The WZ is shown situated within the center opening of the housing 102 and between the first end wall 120 of the housing 104 and the first end of wall 113 of the housing 102. Accordingly, the WZ may have a height WZH which is equal to the diameter d1 of the first interior wall 108 and may have length WZL which is substantially equal to the distance from the first end wall 120 of the housing portion 104 to the first end wall 113 of the housing 102.

Figure 5:
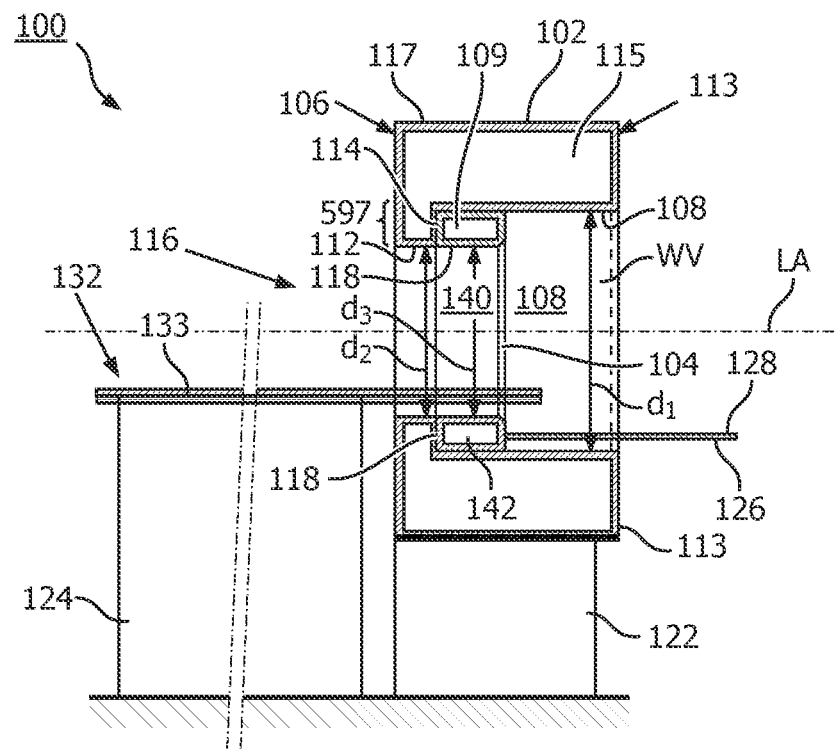
FIG. 5 is a cutaway side view illustration of a portion of the MRI scanner system taken along lines 5-5 of FIG. 2 in accordance with one or more embodiments of the present system.

FIG. 5 is a cutaway side view illustration of a portion of the MRI scanner system 100 taken along lines 5-5 of FIG. 2 in accordance with embodiments of the present system. The cross section of the housing 102 and the housing 104 are axis symmetric. However, the cross section of the housing 102 may be "L" shaped, with the base (i.e., bottom) of the "L" forming at least part of the second end wall 106 and a flanged area 597 of the housing 102. The leg of the "L" may extend substantially between first and second end walls 113 and 106, respectively, of the housing 102. The housing 104 is illustratively situated such that it is adjacent to the leg of the "L". The working volume WV is shown as that volume surrounded by the first inner wall 108 of the housing 102 and situated between the first end wall 113 of the housing 102 and the first end wall 120 of the housing 104. The region of interest (ROI) may be located within the scanning volume surrounded the inner wall 140 of the housing 104 situated between the first and second end walls 220 and 118 of the housing 104. In accordance with embodiments of the present system with systems such as beam forming, beam projection, etc., the ROI may be projected beyond the housing 104, such as beyond the first end wall 120.

Figure 6:
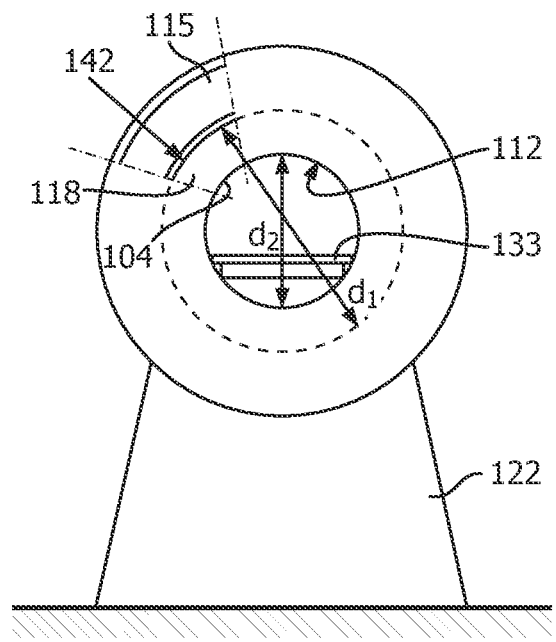
FIG. 6 is a partially cutaway rear view of a portion of an MRI scanner system looking through the second opening in accordance with one or more embodiments of the present system.

FIG. 6 is a partially cutaway rear view of a portion of an MRI scanner system 100 looking through the second opening 116 in accordance with embodiments of the present system. The housing 102 is partially cutaway to reveal the second end wall 118 of the housing 104. For the sake of clarity, only a portion of the patient support 133 is shown.

Figure 7:
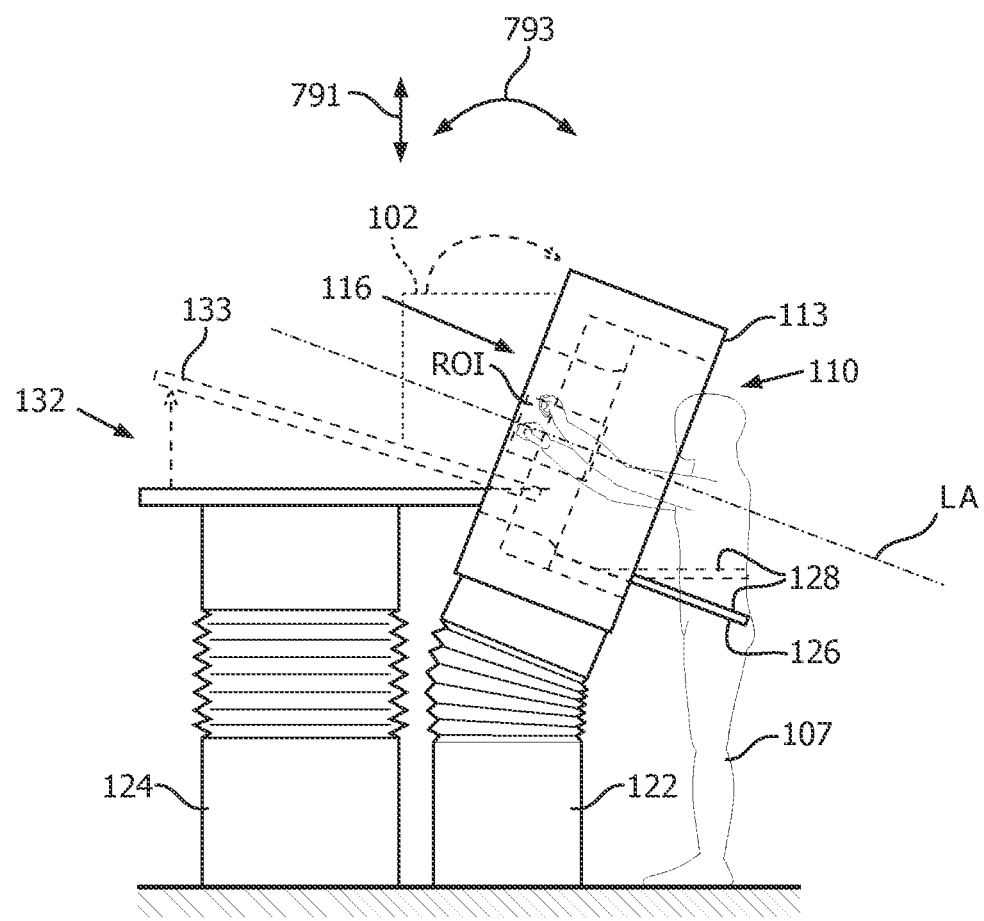
FIG. 7 is a side view of a portion of the MRI scanner system articulated during use in accordance with one or more embodiments of the present system.

FIG. 7 is a side view of a portion of the MRI scanner system 100 articulated during use in accordance with embodiments of the present system. The support 122 may support the housing 101 and may be articulable with one, two or more degrees of freedom (e.g., such as six or more degrees of freedom) so as to position the housing 102 and/or the patient support 132, 133 in one or more desired positions such as a tilted position (e.g., see arrow 793) and raised (e.g., see arrow 791), for example, to provide clearance for the head of the user 107, so that the user 107 may conveniently access the ROI through the first opening 110, the second opening 116, and/or perform an MRGI procedure at the ROI and/or at other locations on the patient 105. Further, by tilting the patent support 132, 133, for example, the user 107 may access the ROI without having to bend over or with minimal bending. In accordance with embodiments of the present system, this may reduce stress upon the user 107 during MRGI procedures and provide higher quality health care. The MRI scanner system 100 may provide real-time image information corresponding to portions of the patient's body 105 at the ROI on a display of the system such as a wearable type display (glasses-type) worn by the user 107 and/or on another display (e.g., see display 930 in FIG. 9). The display may display procedure related information such as the patient blood pressure, etc. However, other displays are also envisioned. Similarly, the patient supports 133 and 126 of the patient support 132 may each be articulable with one, two or more degrees of freedom (e.g., such as with six or more degrees of freedom) so as to position a patient, or body parts thereof, in a desired position for MRGI procedures. The articulation of the patient supports 133 and/or 126 may be determined in accordance with a position of the housing 102 or may be independently determined. For example, a user may set the position of one or more of the patient supports 133 and 126 or the controller may set the position of one or more of the patient supports 133 and 126, such as in accordance with predetermined settings stored in a memory of the system (e.g., in accordance with predetermined MRGI procedures, surgeon information, etc.).

Figure 8:
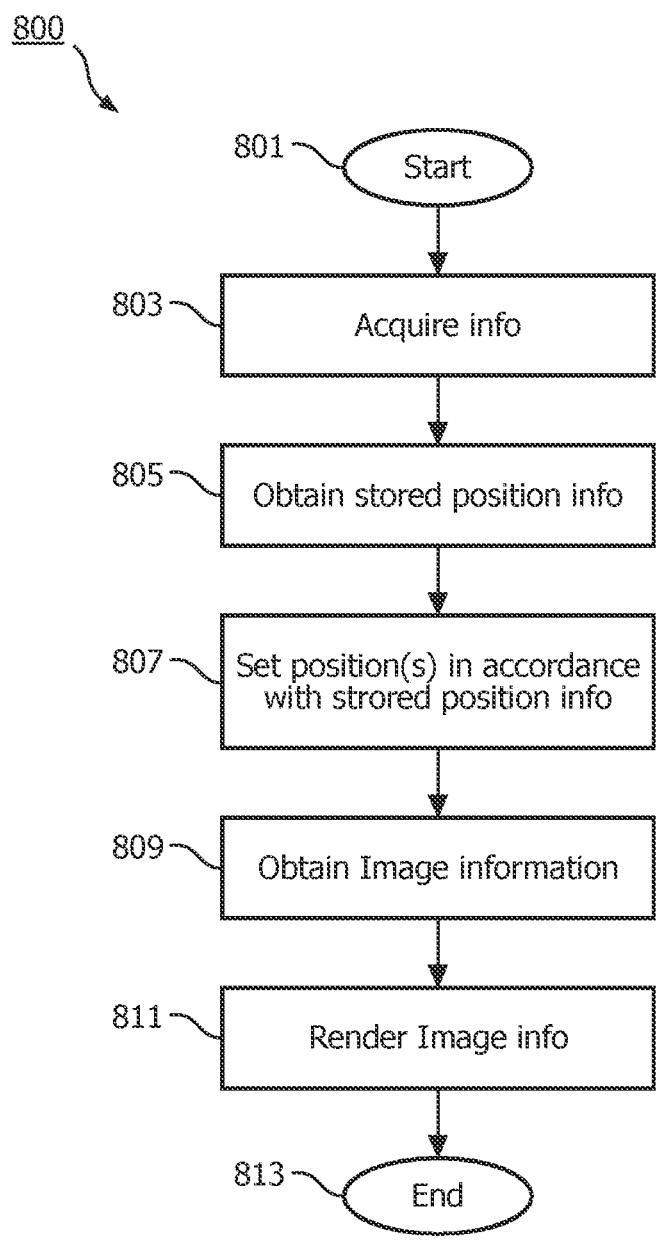
FIG. 8 is a flow diagram that illustrates a process 800 performed on an MRI system in accordance with one or more embodiments of the present system.

FIG. 8 is a flow diagram that illustrates a process 800 performed on an MRI system in accordance with embodiments of the present system. The process 800 may be performed using one or more computers communicating over a network and may obtain information and/or store information using one or more memories which may be local and/or remote from each other. The process 800 may include one of more of the following acts. Further, one or more of these acts may be combined and/or separated into sub-acts, if desired. In operation, the process may start during act 801 and then proceed to act 803.

During act 803, the process may acquire information related to one or more of a MRGI procedure to be performed, surgeon identification (ID), patient information (e.g., patient ID and/or patient body size, etc.), and/or preferred setting information (e.g., tilt override, 5 degrees tilt patient support, position patient support within center volume of the housing 102, etc.). This information may be input electronically or via a user input device of the system such as a user interface (UI) of the system. After completing act 803, the process may continue to act 805.

During act 805, the process may obtain the stored position information corresponding to the information input during act 803 from a memory of the system. The stored position information may include information defining a position of a solenoid coil housing including a working volume, the patient support, etc., corresponding to the information acquired during act 803. For example, if the current MRGI procedure is to be performed by Dr. Smith and is a pelvic procedure, the process may obtain the 10/0/−5/10 stored position information from Table 1 as will be discussed below. The stored position information may include location settings by MRGI procedure type (e.g., lower pelvic, upper pelvic, cranial procedures, etc.), surgeon ID, patient ID, override information, etc. The stored position information may be set and/or updated by a user of the system. For example, a surgeon may update stored position information during an MRGI procedure using any suitable command such as a voice command (e.g., "store current tilt setting for all cranial procedures"), through use of a UI, etc., and the system may (e.g., using a voice activated application) process and respond to the command accordingly. Table 1 illustrates stored position information settings for three types of pelvic procedures Pelvic1 Pelvic2 and Pelvic3.

TABLE 1

| PROCEDURE | DEFAULT | DR DOE | DR SMITH | DR JOHN |
|---|---|---|---|---|
| | TILT (DEG)/HEIGHT (CM)/patient support1/patient support2 | | | |
| PELVIC1 | 5/10 | 5/5 | −5/10 | — |
| PELVIC2 | 10/— | 10/10 | — | 5/−10 |
| PELVIC3 | 10/— | 20/20 | — | — |

With regard to the Pelvic1 procedure in Table 1, the default setting may be 5 degrees of tilt of the first patient support (support1 e.g., see FIGS. 1 133) and 10 degrees of tilt for the second patient support (support2 e.g., see FIG. 1 126). However, for the same procedure, Dr. Doe may desire that the patient supports both be set to 5 degrees of tilt; Dr Smith may desire that the first patient support be set to −5 degrees of tilt and the second patient support be set to 10 degrees of tilt; and Dr. John has a dash entry indicating the preference for the default setting for this procedure. Referring to the Pelvic2 procedure, it is indicated that Dr. John has a preference for the first patient support be set to 5 degrees of tilt and the second patient support be set to −10 degrees of tilt. In a similar manner the patient supports may have height information also associated therewith. With regard to the stored position information, it is also envisioned that this information may be weighted so that, for example, one or more settings of a user may override one or more default settings. Further, the process may include a learning application which may learn a user's preferred settings using current and historical settings obtained during MRGI procedures performed by the corresponding user, patient, physician, etc. After completing act 805, the process may continue to act 807.

During act 807, the process may set positions of the housing and/or patient supports in accordance with the stored position information settings obtained during act 805. Accordingly, the controller may obtain sensor information from one or more position/orientation sensors of the system which may detect positions and/or orientation of the housing and/or patient support(s) (e.g., see support1 and/or support2 above) and may actuate one or more actuators accordingly so that a desired position and/or orientation of the housing and/or patient support(s) is obtained. The system may also include a patient entry or exit routine which may position a patient into the ROI (e.g., at the start of an MRGI procedure) or remove the patient from the ROI (e.g., at the end or during an interval of an MRGI procedure), if desired. The system may also include positioning of surgical instruments, etc., which may enable positioning of the instrument(s), etc., within or outside the ROI (e.g., at the start of an MRGI procedure) or removal/repositioning of the instrument(s) from the ROI (e.g., at the end or during an interval of an MRGI procedure), if desired. After completing act 807, the process may continue to act 809.

During act 809, the process may obtain image information. Accordingly, the process may activate one or more of the first coil, the second coil, the gradient coil, the RF portion, etc. to obtain MRI image information in the ROI as discussed herein. After completing act 809, the process may continue to act 811.

During act 811, the process may render the MR image information obtained during act 809 on a user interface (UI) such as a display of the MRI system. In some embodiments, it is envisioned that the display may include mobile displays such as a wearable display worn on a head of user. After completing act 811, the process may continue to act 813 where it ends.

Figure 9:
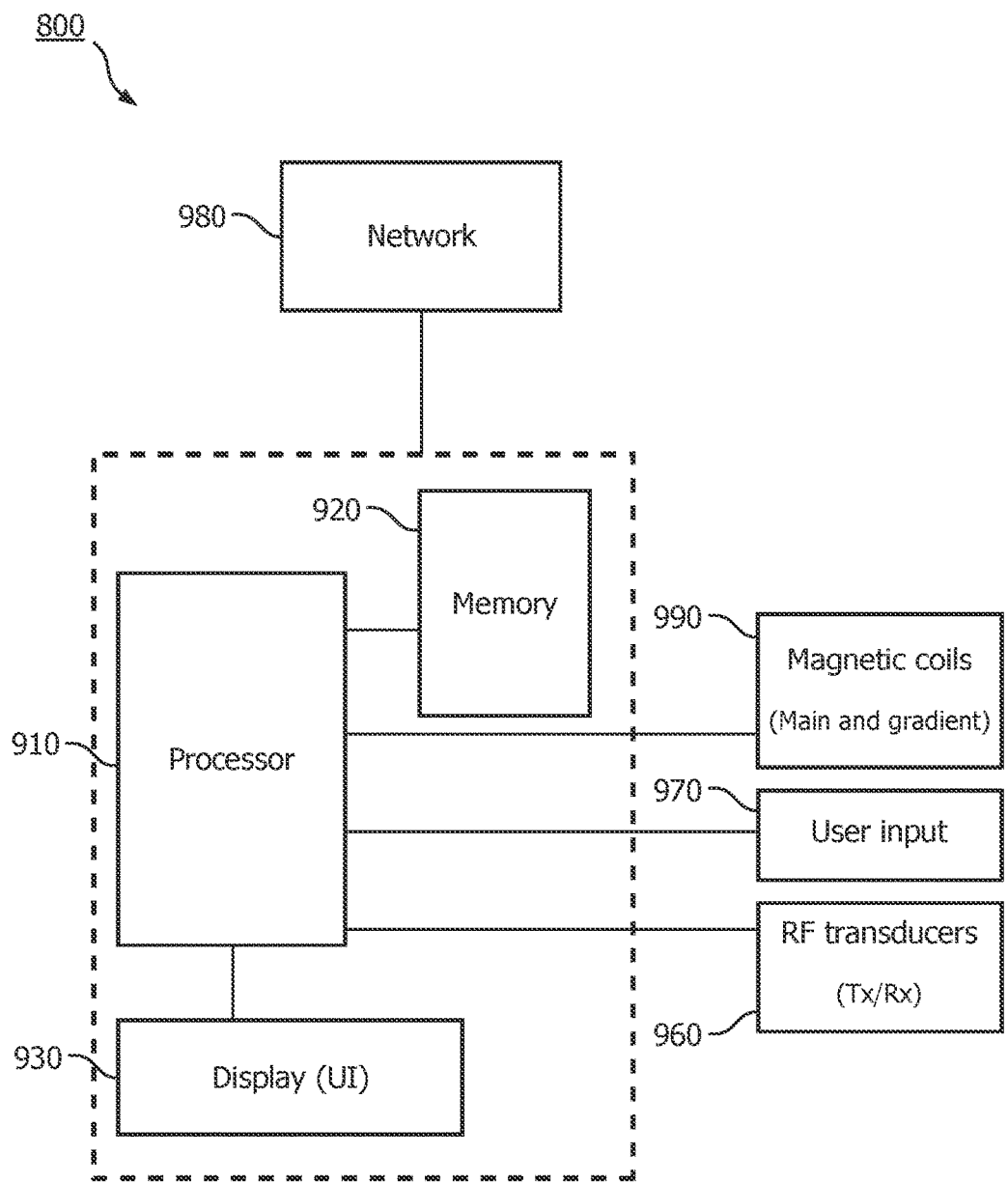
FIG. 9 shows a portion of a system 900 (e.g., peer, server, etc.) in accordance with one or more embodiments of the present system.

FIG. 9 shows a portion of a system 900 (e.g., MRI system, etc.) in accordance with an embodiment of the present system. For example, a portion of the present system may include a processor 910 (e.g., a controller) operationally coupled to a memory 920, a display 930, RF transducers 960, magnetic coils 990, and a user input device 970. The memory 920 may be any type of device for storing application data as well as other data, such as patient support positioning information related to the described operation. The application data and other data are received by the processor 910 for configuring (e.g., programming) the processor 910 to perform operation acts in accordance with the present system. The processor 910 so configured becomes a special purpose machine particularly suited for performing in accordance with embodiments of the present system.

The operation acts may include configuring an MRI system by, for example, controlling one or more of support actuators (e.g., housing support and/or patient supports), the magnetic coils 990, and/or the RF transducers 960. The patient supports may control a physical location (e.g., in x, y, and z axes) of a test subject and the housing supports may control a physical location (e.g., in x, y, and z axes) of the housing. The magnetic coils 990 may include main magnetic coils, and gradient coils (e.g., x-, y-, and z-gradient coils) and may be controlled to emit a main magnetic field and/or gradient fields in a desired direction and/or strength. The controller may control one or more power supplies to provide power to the magnetic coils 990 so that a desired magnetic field is emitted at a desired time. The RF transducers 960 may be controlled to transmit RF pulses at the test subject and/or to receive echo information therefrom. A reconstructor (e.g., the processor) may process received signals such as the echo information and transform them into content which may include image information (e.g., still or video images (e.g., video information)), data, and/or graphs that may be rendered on, for example, a user interface (UI) of the present system such as on one or more of the display 930, etc. Further, the content may then be stored in a memory of the system such as the memory 920 for later use. Thus, operation acts may include positioning of the patient, requesting, providing, and/or rendering of image information such as, for example, reconstructed image information obtained from the echo information. etc. The processor 910 may render the content such as image information (e.g., still image, video, etc.) on a UI of the system such as a display of the system.

The user input 970 may include a keyboard, a mouse, a trackball, or other device, such as a touch-sensitive display, which may be stand alone or be a part of a system, such as part of a personal computer, a personal digital assistant (PDA), a mobile phone, a monitor, a smart- or dumb-terminal, MRI terminal, or other device for communicating with the processor 910 via any operable link. The user input device 970 may be operable for interacting with the processor 910 including enabling interaction within a UI as described herein. Clearly the processor 910, the memory 920, display 930, and/or user input device 970 may all or partly be a portion of a computer system or other device such as an MRI system.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 920 or other memory coupled to the processor 910.

The program and/or program portions contained in the memory 920 may configure the processor 910 to implement the methods, operational acts, and functions disclosed herein. The memories may be distributed, for example between the MRI system, other MRI systems and/or servers, etc., and the processor 910, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 910. With this definition, information accessible through a network, such as the network 980 is still within the memory, for instance, because the processor 910 may retrieve the information from the network for operation in accordance with the present system.

The processor 910 is operable for providing control signals and/or performing operations in response to input signals from the user input device 970 as well as in response to other devices of a network and executing instructions stored in the memory 920. The processor 910 may include one or more of a microprocessor, an application-specific or general-use integrated circuit(s), a logic device, etc. Further, the processor 910 may be a dedicated processor for performing in accordance with the present system or may be a general-purpose processor wherein only one of many functions operates for performing in accordance with the present system. The processor 910 may operate utilizing a program portion, multiple program segments, or may be a hardware device utilizing a dedicated or multi-purpose integrated circuit.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow.

Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated; and i) the term "plurality of" an element includes two or more of the claimed element, and does not imply any particular range of number of elements; that is, a plurality of elements may be as few as two elements, and may include an immeasurable number of elements.

What is claimed is:

1. A magnetic resonance imaging system comprising:
a housing having first and second openings and an interior cavity defined by first, second and third interior walls, first and a second solenoid coils, and
a patient support situated at least partly within the first and second openings of the housing and including at least one slidable articulating section configured to insert a patient into a region of interest,
wherein the first and second solenoid coils are arranged to generate a magnetic field suitable for imaging within the region of interest,
wherein the first and second solenoid coils have a common longitudinal axis,
wherein the first and second openings are situated on opposite sides of the housing along the longitudinal axis,
wherein the first opening is larger than the second opening,
wherein the first solenoid coil have a larger inside diameter than the second solenoid coil and are positioned adjacent the first opening, and the second solenoid coil is positioned adjacent the second opening,
wherein the housing has an "L" shaped cross section including the second interior wall forming at least part of the second opening and the first interior wall forming at least part of the first opening and the third interior wall extending between the first interior wall and the second interior wall,
wherein the region of interest is located within a scanning volume surrounded by the first interior wall that forms the at least part of the first opening, and
wherein the patient support is configured to articulate in one or more directions under the control of one or more of a controller and manual operation.

2. The apparatus of claim 1, wherein the patient support further comprises a further patient support situated at least in part within the first opening and having a bifurcated end extending from the first opening.

3. The apparatus of claim 1, the housing having a length, and an exterior periphery defined by an exterior wall wherein the third interior wall radially extends between the first and second interior walls.

4. The apparatus of claim 3, further comprising at least one gradient coil, situated adjacent to the third interior wall.

5. The apparatus of claim 1, further comprising a controller configured to control patient positioning in coordination with image reconstruction.

6. The apparatus of claim 1, further comprising a display situated within the interior of the housing and configured to render procedure related information.

7. The apparatus of claim 1, comprising at least one asymmetric gradient coil situated between at least one of the solenoid coils and the patient.

8. The apparatus of claim 1, further including:
a second patient support having bifurcated ends for access to the first opening.

9. A solenoid structure for a magnetic resonance imaging system, comprising:
a closed solenoid structure comprising a housing having first and second openings and an interior cavity defined by first, second and third interior walls, the closed solenoid structure further comprising first and second solenoid coils disposed in the housing and each having a common longitudinal axis;
a support which supports the housing of the closed solenoid structure; and
a first patient support situated at least partly within the first and second openings of the housing and configured to insert a patient into a region of interest;
a second patient support having bifurcated ends for access to the first opening;
wherein each coil is configured to provide a homogenous magnetic field for imaging in the region of interest,
wherein the first and second openings are situated on opposite sides of the closed solenoid structure along the longitudinal axis and having different diameters, wherein the first opening is larger than the second opening,
wherein the first solenoid coil has a different inside diameter than the second solenoid coil and is positioned adjacent the first opening, and the second solenoid coil and is positioned adjacent the second opening,
wherein the closed solenoid structure has an "L" shaped cross section including the second interior wall forming at least part of the second opening and the first interior wall forming at least part of the first opening,
wherein the region of interest is located within a scanning volume surrounded by the first interior wall that forms the at least part of the first opening.

10. The solenoid structure of claim 9, wherein the first and second openings have a circular cross section in a plane perpendicular to the longitudinal axis.

11. The solenoid structure of claim 9, wherein the patient support is configured to position a patient into a desired position of a plurality of positions under the control of a one or more of a controller and manual operation.

12. The solenoid structure of claim 9 wherein the support which supports the housing of the closed solenoid structure is controllable to tilt the closed solenoid structure to a desired position.

13. The solenoid structure of claim 9 wherein the support which supports the housing of the closed solenoid structure includes one or more hydraulic, electronic, pneumatic, or mechanical actuators controllable to tilt the closed solenoid structure to a desired position.

14. The solenoid structure of claim 9, wherein the first patient support includes at least one articulating section slidable to insert a patient into a region of interest.

15. A magnetic resonance imaging system comprising:
a housing having a larger first opening and a smaller second opening on opposite sides of the housing wherein the larger first opening is larger than the smaller second opening, the housing further having an interior cavity defined in part by larger diameter first interior wall and a smaller diameter second interior wall wherein the larger diameter first interior wall has a larger diameter than the smaller diameter second interior wall, the interior cavity further defined by a third interior wall extending between the first interior wall and the second interior wall;

a first solenoid coil and a second solenoid coil having a common longitudinal axis, the first solenoid coil disposed inside the housing around the larger diameter first interior wall and the second solenoid coil disposed inside the housing around the smaller diameter second interior wall, wherein the first solenoid coil and the second solenoid coil are arranged to generate a magnetic field suitable for imaging within a region of interest that is surrounded by the larger diameter first interior wall;

a support which supports the housing wherein the support includes one or more hydraulic, electronic, pneumatic, or mechanical actuators controllable to tilt the housing to a desired position; and a patient support configured to insert a patient into the region of interest.

16. The magnetic resonance imaging system of claim 15 wherein the first solenoid coil has a larger inside diameter than the second solenoid coil.

17. The magnetic resonance imaging system of claim 15 wherein the patient support includes:

a stationary patient support extending outside of the smaller second opening of the housing; and a movable patient support configured to move the patient over the stationary patient support to enter the region of interest through one of the larger first opening or the smaller second opening of the housing.

18. The magnetic resonance imaging system of claim 17 wherein the patient support has an opening at the larger first opening of the housing providing user access to the region of interest.

19. The magnetic resonance imaging system of claim 15, wherein the patient support includes:

a first patient support situated at least partly within the first and second openings of the housing and including at least one slidable articulating section configured to insert a patient into a region of interest.

20. The magnetic resonance imaging system of claim 19, wherein the patient support includes:

a second patient support having bifurcated ends for access to the first opening.

* * * * *